United States Patent [19]

Muller et al.

[11] Patent Number: 6,020,358

[45] Date of Patent: Feb. 1, 2000

[54] SUBSTITUTED PHENETHYLSULFONES AND METHOD OF REDUCING TNFα LEVELS

[75] Inventors: George W. Muller, Bridgewater; Hon-Wah Man, Neshanic Station, both of N.J.

[73] Assignee: Celgene Corporation, Warren, N.J.

[21] Appl. No.: 09/183,049

[22] Filed: Oct. 30, 1998

[51] Int. Cl.[7] .................. A61K 31/40; C07D 209/46; C07D 209/48; C07D 209/56

[52] U.S. Cl. .................. 514/411; 514/416; 514/417; 514/309; 514/372; 548/451; 548/472; 548/478; 548/209; 546/141

[58] Field of Search .................. 548/472, 478, 548/451; 514/416, 417, 411

[56] References Cited

U.S. PATENT DOCUMENTS

| | | | |
|---|---|---|---|
| 4,173,652 | 11/1979 | Bruins et al. | 424/324 |
| 4,556,673 | 12/1985 | Anderson et al. | 514/414 |
| 4,820,828 | 4/1989 | Demers et al. | 549/362 |
| 5,658,940 | 8/1997 | Muller et al. | 514/417 |

FOREIGN PATENT DOCUMENTS

| | | |
|---|---|---|
| WO 97/05105 | 2/1997 | WIPO. |
| WO 97/24117 | 7/1997 | WIPO. |

OTHER PUBLICATIONS

Corral, Laura G., et al. (Jul. 1996), "Selection of Novel Analogs of Thalidomide with Enhanced Tumor Necrosis Factor alpha Inhibitory Activity", Molecular Medicine, vol. 2, No. 4, pp. 506–515, Jul. 1996.

A. De, U. et al., (Feb. 1975), "Possible Antineoplastic Agents I", Journal of Pharmaceutical Sciences, vol. 64(2), pp. 262–266.

Barnes, P.J., (1995) "Cyclic nucleotides and phosphodiesterases and airway function", Eur Respir. J. vol. 8, pp. 457–462.

Bazzoni, Flavia, et al., (Jun. 26, 1996), "The Tumor Necrosis Factor Ligand And Receptor Families", Seminars in Medicine of the Beth Israel Hospital, Boston, Flier, Jeffrey S., et al, Ed., vol. 334, No. 26, pp. 1717–1725.

Burnouf, Catherine, et al., (1998), "Chapter 10: Phosphodiesterases 4 Inhibitors", Annual Reports in Medicinal Chemistry, Doherty, Ed., vol. 33, pp. 91–109.

Buu–Ho, Nouyen P. et al., (Mar. 1970), "Synthesis and Pharmacological Properties of Substituted Cinnamohydroxamic Acids", JMC, vol. 13(2), pp. 211–213.

Badger, Alison M. et al., (Oct. 1997), "Advances in antiarthritic therapeutics", DDT, vol. 2, No. 10, pp. 427–435.

Beutler, Bruce et al., (1993), "Tumor Necrosis Factor in the pathogenesis of infectious diseases", Critical Care Medicine, vol. 21, No. 10, pp. S423–S435.

deBrito, FB et al., (1997) "Type 4 Phosphodiesterase Inhibitors and their Potential in the Treatment of Inflammatory Disease", Emerging Drugs, vol. 2, Chapter Twelve pp. 249–268.

Denis, L.J., et al., (1997) "Matrix Metalloproteinase Inhibitors: Present Achievements and Future Prospects", Investigational New Drugs, vol. 15, pp. 175–185.

Eger, K. et al., (1990), "Synthesis, Central Nervous System Activity and Teratogenicity of a Homothalidomide", Arzneim–Forsch/Drug Res, vol. 40(II), No. 10 pp. 1073–1975.0.

Friderichs, Von E., (1982), "Untersuchungen zum ZNS–Wirkprofil von Thalidomid–Analoga", Arzhelm–Forsch./Drug Res., vol. 32(1), No. 6, pp. 613–620.

Hart, David J. et al., (1983) "Preparation of Primary Amines and 2–Azetidinones via N–Trimethylsilyl Imines", J. Org. Chem., vol. 48, pp. 289–294.

Hughes, Bernadette, et al., (Mar. 1997) "PDE 4 inhibitors: the use of molecular cloning in the design and development of novel drugs", DDT, vol. 2, No. 3, pp. 89–101.

Kleinman, Edward F., et al., (1998), "Striking Effect of Hydroxamic Acid Substitution on the Phosphodiesterase Type 4 (PDE4) and TNF α Inhibitory Activity of Two Series of Rolipram Analogues: Implications for a New Active Site Model of PDE4.", J. Med. Chem., vol. 41, pp. 266–270.

Lombardo, Louis J., (Sep. 1995), "Anti–Inflammatory & Anti–Allergy Agents", Current Pharmaceutical Design, Weichman, Barry M., Ed., vol. 1, No. 2, pp. 255–268.

Lee, John C. et al., (1995), "Low–Molecular–Weight TNF Biosynthesis Inhibitors: Strategies and Prospectives", Circulatory Shock, vol. 44, pp. 97–103.

Levy, Daniel E., et al., (1998), Matrix Metalloproteinase Inhibitors: A Structure–Activity Study, J. Med Chem., vol. 41, pp. 199–223.

Müller, Thomas et al., (Aug. 1996) "Subtypes of the type 4 cAMP phosphodiesterases: structure, regulation and selective inhibition", TIPS, vol. 17, pp. 294–298.

Marriott, J. Blake, (1997), "TNF–α antagonists: monoclonal antibodies, soluble receptors, thalidomide and other novel approaches", Exp. Opin. Invest. Drugs, vol. 6(8), pp. 1105–1108.

Muller, George W., et al, (1998), "Thalidomide Analogs and PDE4 Inhibition", Bioorganic & Medicinal Chemistry Letters, vol. 8, pp. 2669–2674.

Muller, George W., et al. (1996), "Structural Modifications of Thalidomide Produce Analogs with Enhanced Tumor Necrosis Factor Inhibitory Activity", Journal of Medicinal Chemistry, vol. 39, No. 17, pp. 3238–3240.

Natchus, Michael G., et al., (1998), "Design and Synthesis of Conformationally–Constrained MMP Inhibitors", Bioorganic & Medicinal Chemistry Letters, vol. 8, pp. 2077–2080.

(List continued on next page.)

Primary Examiner—Laura L. Stockton
Attorney, Agent, or Firm—Mathews, Collins, Shepherd & Gould

[57] ABSTRACT

Phenethylsulfones substituted in the position α to the phenyl group with a 1-oxoisoindoline or 1,3-dioxoisoindoline group reduce the levels of TNFα in a mammal. Typical embodiments are 2-[1-(3-ethoxy-4-methoxyphenyl)-2-methylsulfonylethyl]-4-aminoisoindoline-1,3-dione and 2-[1-(3-cyclopentyloxy-4-methoxyphenyl)-2-methylsulfonylethyl]isoindoline-1,3-dione.

19 Claims, No Drawings

OTHER PUBLICATIONS

Naafs, B., et al., (Mar. 1985), "Thalidomide Therapy, An Open Trial", *International Journal of Dermatology,* vol. 24(2), pp. 131–134.

Palfreyman, Malcolm N., (1995) "Phosphodiesterase type IV inhibitors as Anti–Inflammatory agents", *Drugs of the Future,* vol. 30(8), pp. 793–804.

Palacios, Jose Maria, et al., (1995), "Second Messenger Systems as Targets for New Therapeutic Agents: Focus on Selective Phosphodiesterase Inhibitors", *Il Farmaco,* vol. 50(12), pp. 819–827.

Summers, James B., et al, (1998), "Matrix Metalloproteinase Inhibitors and Cancer", *Annual Reports In Medicinal Chemistry,* vol. 33, pp. 131–140.

Steinman, Douglas H. et al, (1998), "The Design, Synthesis, and Structure–Activity Relationships of a Series of Macrocyclic MMP Inhibitors", *Bioorganic & Medicinal Chemistry Letters,* vol. 8, pp. 2087–2092.

Strieter, Robert M. et al., (1993), "Role of tumor necrosis factor–α in disease states and inflammation", *Critical Care Medicine,* vol. 21, No. 10, pp. S447–S463.

Torphy, Theodore J. et al., (May 1993) "Novel Phosphodiesterase Inhibitors for the Therapy of Asthma", *DN&P* vol. 6(4), pp. 203–214.

Torphy, Theodore J. et al., (1998) "Phosphodiesterase Isozymes, Molecular Targets for Novel Antiasthma Agents", *Am J. Resp. Crit. Care Med.,* vol. 157, pp. 351–370.

Torphy, Theodore J., (1997), "Phosphodiesterase Inhibitors", *Asthma,* Barnes, P.J. et al., pp. 1755–1773.

Teixeira, Mauro M. et al., (May 1997) "Phosphodiesterase (PDE)4 inhibitors:anti–inflammatory drugs of the future", *TIPS,* vol. 18, pp. 164–170.

Tracey, Kevin J. et al, (1993), "Tumor Necrosis Factor, Other Cytokines and Disease", *Annu. Rev. Cell Biol.* vol. 9, pp. 317–343.

Tanaka, Kuntyoshi, et al., (1983), "Syntheses and Anti–Inflammatory and Analgesic Activities of Hydroxamic Acids and Acid Hydrazides", *Chem. Pharm. Bull,* vol. 31(8), pp. 2810–2819.

Wojtowicz–Praga, Slawomir M., et al., (1997), "Matrix Metalloproteinase Inhibitors", *Investigational New Drugs,* vol. 15, pp. 61–75.

Yu, Anita E., et al., (Sep. 1997), "Matrix Metalloproteinases, Novel Targets for Directed Cancer Therapy", *Drugs & Aging,* vol. 11(3), pp. 229–244.

SUBSTITUTED PHENETHYLSULFONES AND METHOD OF REDUCING TNFα LEVELS

The present invention relates to substituted phenethylsulfones substituted α to the phenyl group with a 1-oxoisoindoline group, the method of reducing levels of tumor necrosis factor α and treating inflammatory and autoimmune diseases in a mammal through the administration thereof, and to pharmaceutical compositions of such derivatives.

BACKGROUND OF THE INVENTION

Tumor necrosis factor α, or TNFα, is a cytokine which is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endotoxemia and/or toxic shock syndrome {Tracey et al., Nature 330, 662–664 (1987) and Hinshaw et al., Circ. Shock 30, 279–292 (1990)}; rheumatoid arthritis, Crohn's disease, IBD, cachexia {Dezube et al., Lancet, 335 (8690), 662 (1990)} and Adult Respiratory Distress Syndrome where TNFα concentration in excess of 12,000 pg/mL have been detected in pulmonary aspirates from ARDS patients {Millar et al., Lancet 2(8665), 712–714 (1989)}. Systemic infusion of recombinant TNFα also resulted in changes typically seen in ARDS {Ferrai-Baliviera et al., Arch. Surg. 124(12), 1400–1405 (1989)}.

TNFα appears to be involved in bone resorption diseases, including arthritis. When activated, leukocytes will produce bone-resorption, an activity to which the data suggest TNFα contributes. {Bertolini et al., Nature 319, 516–518 (1986) and Johnson et al., Endocrinology 124(3), 1424–1427 (1989)}. TNFα also has been shown to stimulate bone resorption and inhibit bone formation in vitro and in vivo through stimulation of osteoblast formation and activation combined with inhibition of osteoblast function. Although TNFα may be involved in many bone resorption diseases, including arthritis, a most compelling link with disease is the association between production of TNFα by tumor or host tissues and malignancy associated hypercalcemia {Calci. Tissue Int. (US) 46(Suppl.), S3–10 (1990)}. In Graft versus Host Reaction, increased serum TNFα levels have been associated with major complication following acute allogenic bone marrow transplants {Holler et al., Blood, 75(4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., N. Engl. J. Med. 320(24), 1586–1591 (1989)}.

Macrophage-induced angiogenesis is known to be mediated by TNFα. Leibovich et al. {Nature, 329, 630–632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth. TNFα production also has been associated with cancerous conditions, particularly induced tumors {Ching et al., Brit. J. Cancer, (1955) 72, 339–343, and Koch, Progress in Medicinal Chemistry, 22, 166–242 (1985)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., Nature, 344:245–247 (1990)}. High levels of TNFα production (in the serum and in isolated macrophages) have been demonstrated in animal models of silica and asbestos induced fibrosis {Bissonnette et al., Inflammation 13(3), 329–339 (1989)}. Alveolar macrophages from pulmonary sarcoidosis patients have also been found to spontaneously, release massive quantities of TNFα as compared with macrophages from normal donors {Baughman et al., J. Lab. Clin. Med. 115(1), 36–42 (1990)}.

TNFα is also implicated in the inflammatory response which follows reperfusion, called reperfusion injury, and is a major cause of tissue damage after loss of blood flow {Vedder et al., PNAS 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., J. Cell Biol. 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., Am. J Path. 135(1), 121–132 (1989)}.

TNFα blockage with monoclonal anti-TNFα antibodies has been shown to be beneficial in rheumatoid arthritis {Elliot et al., Int. J. Pharmac. 1995 17(2), 141–145} and Crohn's disease {von Dullemen et al., Gastroenterology, 1995 109(1), 129–135}

Moreover, it now is known that TNFα is a potent activator of retrovirus replication including activation of HIV-1. {Duh et al., Proc. Nat. Acad. Sci. 86, 5974–5978 (1989); Poll et al., Proc. Nat. Acad. Sci. 87, 782–785 (1990); Monto et al., Blood 79, 2670 (1990); Clouse et al., J. Immunol. 142, 431–438 (1989); Poll et al., AIDS Res. Hum. Retrovirus, 191–197 (1992)}. AIDS results from the infection of T lymphocytes with Human Immunodeficiency Virus (HIV). At least three types or strains of HIV have been identified; i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., *The Immunopathogenesis of HIV Infection*, Advances in Immunology, 57 (1989)}. Cytokines, such as TNFα, have been shown to activate HIV replication in monocytes and/or macrophages {Poli et al., *Proc. Natl. Acad Sci.*, 87, 782–784 (1990)}; therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osbom, et al., *PNAS* 86 2336–2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., *PNAS* 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336–2340 (1989)}. TNFα in AIDS associated cachexia is suggested by elevated serum TNFα and high levels of spontaneous TNFα production in peripheral blood monocytes from patients (Wright et al., *J. Immunol.* 141(1), 99–104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., *Cell* 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al., *J Biol. Chem.* 1993, 17762–66; Duh et al., *Proc. Natl. Acad. Sci.* 1989, 86, 5974–78; Bachelerie et al., *Nature* 1991, 350, 709–12; Boswas et al., *J Acquired Immune Deficiency Syndrome* 1993, 6, 778–786; Suzuki et al., *Biochem. And Biophys. Res. Comm.* 1993, 193, 277–83; Suzuki et al., *Biochem. And Biophys. Res. Comm.* 1992, 189, 1709–15; Suzuki et al., *Biochem. Mol. Bio. Int.* 1993, 31(4), 693–700; Shakhov et al., *Proc. Natl. Acad. Sci. USA* 1990, 171, 35–47; and Staal et al., *Proc. Natl. Acad Sci. USA* 1990, 87, 9943–47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, cancer, septic shock, sepsis, endotoxic shock, graft versus host disease, wasting, Crohn's disease, inflammatory bowel disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, *Drugs of the Future*, 17(9), 799–807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle.

The primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.*, 11, 150–155, 1990). There are seven known members of the family of PDEs. It is recognized, for example, that the inhibition of PDE type IV is particularly effective in both the inhibition of inflammatory mediator release and the relaxation of airway smooth muscle (Verghese, et al., *Journal of Pharmacology and Experimental Therapeutics*, 272(3), 1313–1320, 1995). Thus, compounds that inhibit PDE IV specifically, would exhibit the desirable inhibition of inflammation and relaxation of airway smooth muscle with a minimum of unwanted side effects, such as cardiovascular or anti-platelet effects. Currently used PDE IV inhibitors lack the selective action at acceptable therapeutic doses. The compounds of the present invention are useful in the inhibition of phosphodiesterases, particularly PDE III and PDE IV, and in the treatment of disease states mediated thereby.

Decreasing TNFα levels, increasing cAMP levels, and inhibiting PDE IV thus constitute valuable therapeutic strategies for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Prior efforts directed to the suppression of the effects of TNFα have ranged from the utilization of steroids such as dexamethasone and prednisolone to the use of both polyclonal and monoclonal antibodies {Beutler et al., *Science* 234, 470–474 (1985); WO 92/11383}.

DETAILED DESCRIPTION

The present invention is based on the discovery that certain classes of non-polypeptide compounds more fully described herein decrease the levels of TNFα.

In particular, the invention pertains to phenethylsulfone compounds of Formula I:

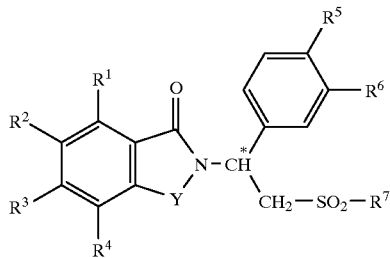

in which
- the carbon atom designated * constitutes a center of chirality;
- Y is C=O, CH2, SO$_2$, or CH$_2$C=O;
- each of R$^1$, R$^2$, R$^3$, and R$^4$, independently of the others, is hydrogen, halo, alkyl of 1 to 4 carbon atoms, alkoxy of 1 to 4 carbon atoms, nitro, cyano, hydroxy, or —NR$^8$R$^9$; or any two of R$^1$, R$^2$, R$^3$, and R$^4$ on adjacent carbon atoms, together with the depicted phenylene ring are naphthylidene;
- each of R$^5$ and R$^6$, independently of the other, is hydrogen, alkyl of 1 to 4 carbon atoms, alkoxy of 1 to 4 carbon atoms, cyano, or cycloalkoxy of up to 18 carbon atoms;
- R$^7$ is hydroxy, alkyl of 1 to 8 carbon atoms, phenyl, benzyl, or NR$^{8'}$R$^{9'}$;
- each of R$^8$ and R$^9$ taken independently of the other is hydrogen, alkyl of 1 to 8 carbon atoms, phenyl, or benzyl, or one of R$^8$ and R$^9$ is hydrogen and the other is —COR$^{10}$ or —SO$_2$R$^{10}$, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and
- each of R$^{8'}$ and R$^{9'}$ taken independently of the other is hydrogen, alkyl of 1 to 8 carbon atoms, phenyl, or benzyl, or one of R$^{8'}$ and R$^{9'}$ is hydrogen and the other is —COR$^{10'}$ or —SO$_2$R$^{10'}$, or R$^{8'}$ and R$^{9'}$ taken together are tetramethylene, pentamethylene, hexamethylene, or —CH$_2$CH$_2$X$^2$CH$_2$CH$_2$— in which X$^2$ is —O—, —S—, or —NH—.

It will be appreciated that while for convenience the compounds of Formula I are identified as phenethylsulfones, they include sulfonamides when R$^7$ is NR$^{8'}$R$^{9'}$.

The term alkyl denotes a univalent saturated branched or straight hydrocarbon chain containing from 1 to 8 carbon atoms. Representative of such alkyl groups are methyl, ethyl, propyl, isopropyl, butyl, isobutyl, sec-butyl, and tert.-butyl. Alkoxy refers to an alkyl group bound to the remainder of the molecule through an ethereal oxygen atom. Representative of such alkoxy groups are methoxy, ethoxy, propoxy, isopropoxy, butoxy, isobutoxy, sec-butoxy, and tert.-butoxy.

The term cycloalkyl as used herein denotes a univalent cyclic hydrocarbon chain which may be saturated or unsaturated. Unless otherwise stated, such chains can contain up to 18 carbon atoms and include monocycloalkyl, polycycloalkyl, and benzocycloalkyl structures. Monocycloalkyl refers to groups having a single ring group. Polycycloalkyl denotes hydrocarbon systems containing two or more ring systems with one or more ring carbon atoms in common; i.e., a spiro, fused, or bridged structure. Benzocycloalkyl signifies a monocyclic alkyl group fused to a benzo group. Representative of monocycloalkyl groups are cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, and cyclooctadecyl. Representative of polycycloalkyl include decahydronaphthalene, spiro[4.5]decyl, bicyclo[2.2.1]heptyl, bicyclo[3.2.1]octyl, pinanyl, norbornyl, and bicyclo[2.2.2]octyl. Benzocycloalkyl is typified by tetrahydronaphthyl, indanyl, and 1.2-benzocycloheptanyl. Cycloalkoxy refers to a cycloalkyl group as just described, that is a monocycloalkyl, polycycloalkyl, or benzocycloalkyl structure, bound to the remainder of the molecule through an ethereal oxygen atom.

It will be appreciated that by the term "sulfone" is used in a generic sense to included not only compounds of Formula I in which R$^7$ is alkyl, phenyl, benzyl, but also the corresponding sulfonic acids when R$^7$ is hydroxy, and sulfonamides when R$^7$ is NR$^{8'}$R$^{9'}$.

A first preferred group of compounds are those of Formula I in which Y is C=O.

A further preferred group of compounds are those of Formula I in which Y is CH$_2$.

A further preferred group of compounds are those of Formula I in which each of R$^1$, R$^2$, R$^3$, and R$^4$ independently of the others, is hydrogen, halo, methyl, ethyl, methoxy, ethoxy, nitro, cyano, hydroxy, or —NR$^8$R$^9$ in which each of R$^8$ and R$^9$ taken independently of the other is hydrogen or methyl or one of R$^8$ and R$^9$ is hydrogen and the other is —COCH$_3$.

A further preferred group of compounds are those of Formula I in which one of R$^1$, R$^2$, R$^3$ and R$^4$ is —NH$_2$ and the remaining of R$^1$, R$^2$, R$^3$ and R$^4$ are hydrogen.

A further preferred group of compounds are those of Formula I in which one of R$^1$, R$^2$, R$^3$, and R$^4$ is —NHCOCH$_3$ and the remaining of R$^1$, R$^2$, R$^3$ and R$^4$ are hydrogen.

A further preferred group of compounds are those of Formula I in which one of R$^1$, R$^2$, R$^3$, and R$^4$ is —N(CH$_3$)$_2$ and the remaining of R$^1$, R$^2$, R$^3$ and R$^4$ are hydrogen.

A further preferred group of compounds are those of Formula I in which one of R$^1$, R$^2$, R$^3$, and R$^4$ is methyl and the remaining of R$^1$, R$^2$, R$^3$, and R$^4$ are hydrogen.

A further preferred group of compounds are those of Formula I in which one of R$^1$, R$^2$, R$^3$, and R$^4$ is fluoro and the remaining of R$^1$, R$^2$, R$^3$, and R$^4$ are hydrogen.

A further preferred group of compounds are those of Formula I in which each of R$^5$ and R$^6$, independently of the other, is hydrogen, methyl, ethyl, propyl, methoxy, ethoxy, propoxy, cyclopentoxy, or cyclohexoxy.

A further preferred group of compounds are those of Formula I in which R$^5$ is methoxy and R$^6$ is monocycloalkoxy, polycycloalkoxy, and benzocycloalkoxy.

A further preferred group of compounds are those of Formula I in which R$^5$ is methoxy and R$^6$ is ethoxy.

A further preferred group of compounds are those of Formula I in which R$^7$ is hydroxy, methyl, ethyl, phenyl, benzyl, or NR$^{8'}$R$^{9'}$ in which each of R$^{8'}$ and R$^{9'}$ taken independently of the other is hydrogen or methyl.

A further preferred group of compounds are those of Formula I in which R$^7$ is methyl, ethyl, phenyl, benzyl or NR$^{8'}$R$^{9'}$ in which each of R$^{8'}$ and R$^{9'}$ taken independently of the other is hydrogen or methyl.

A further preferred group of compounds are those of Formula I in which R$^7$ is methyl.

A further preferred group of compounds are those of Formula I in which R$^7$ is NR$^{8'}$R$^{9'}$ in which each of R$^{8'}$ and R$^{9'}$ taken independently of the other is hydrogen or methyl.

The compounds of Formula I are used, under the supervision of qualified professionals, to inhibit the undesirable effects of TNFα and PDE IV. The compounds can be administered orally, rectally, or parenterally, alone or in combination with other therapeutic agents including antibiotics, steroids, etc., to a mammal in need of treatment.

The compounds also can be used topically in the treatment or prophylaxis of topical disease states mediated or exacerbated by excessive TNFα and PDE IV production, respectively, such as viral infections, such as those caused by the herpes viruses, or viral conjunctivitis, psoriasis, atopic dermnatitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anemia virus, caprine arthritis virus, visna virus, and maedi virus, as well as other lentiviruses.

In a first embodiment, the isoindolinone compounds of the present invention in which Y is C=O can be prepared through reaction of an appropriately substituted phthalic anhydride and a substituted ethylamine:

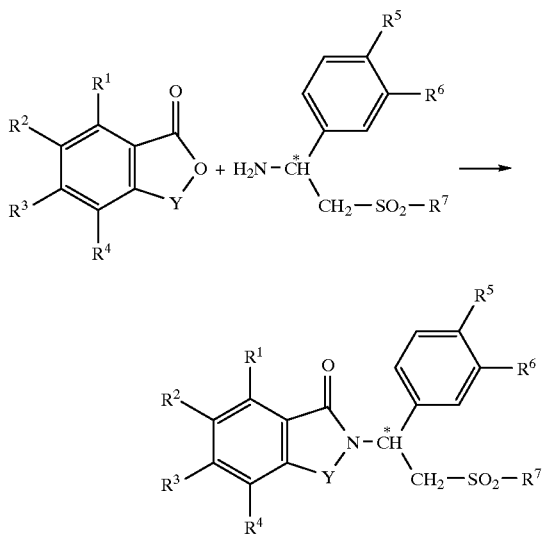

The two reagents are simply heated together, with or without a solvent, and the product isolated and purified by conventional means such as chromatography. When one of $R^1, R^2, R^3$, and $R^4$ is to be amino in the final sulfone, it often is desirable to utilize the corresponding nitro compound in the reaction of the phthalic anhydride and substituted ethylamine and then catalytically convert the resulting nitroisoindolinone after formation. Alternatively, amino groups and other groups which may react can be converted to an appropriately protected group.

In a further embodiment, the isoindolinone compounds of the present invention in which Y is $CH_2$ can be prepared through reaction of an appropriately substituted phthalic dicarboxaldehyde and a substituted ethylamine:

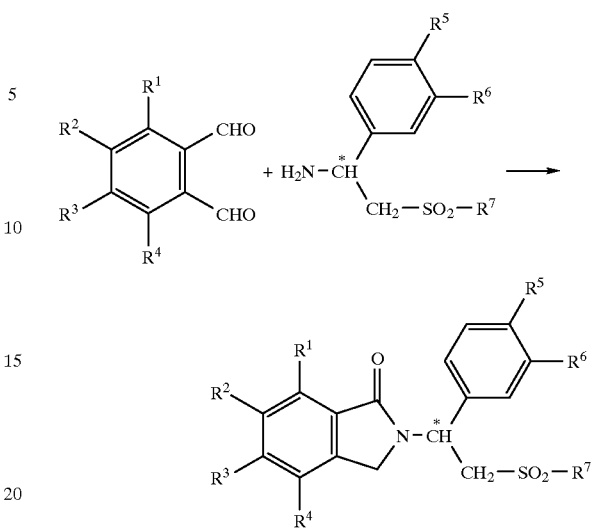

Again the reagents need only be heated together, with or without a solvent, and the product isolated and purified by conventional means such as chromatography. As in the case of the phthalic anhydride used in the first embodiment, if one of $R^1, R^2, R^3$ and $R^4$ is to be amino in the final sulfone, the corresponding nitro compound is used and the resulting nitroisoindolinone then catalytically reduced. Alternatively, one can employ an appropriately protected group, both for amino groups and for any other groups which may react.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed at a later stage of the synthesis and compounds bearing such protecting groups thus are of importance primarily as chemical intermediates (although some derivatives also exhibit biological activity). Accordingly the precise structure of the protecting group is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. 1, Schröder and Lubke, Academic Press, London and New York, 1965; "Methoden der organischen Chemie", Houben-Weyl, 4th Edition, Vol. 15/1, Georg Thieme Verlag, Stuttgart 1974, the disclosures of which are incorporated herein by reference.

An amino group can be protected as an amide utilizing an acyl group which is selectively removable under mild conditions, especially benzyloxycarbonyl, formyl, or a lower alkanoyl group which is branched in 1- or α-position to the carbonyl group, particularly tertiary alkanoyl such as pivaloyl, a lower alkanoyl group which is substituted in the position a to the carbonyl group, as for example trifluoroacetyl.

Coupling agents include such reagents as dicyclohexylcarbodimide and N,N' carbonyldimiidazole.

The compounds of Formula I possess a center of chirality and can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral absorbant. Alternatively, the individual isomers can be prepared in chiral form or separated chemically from a mixture by forming salts with a chiral acid, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

The present invention also pertains to the physiologically acceptable non-toxic acid addition salts of the compounds of Formula I. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of the present invention associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

The following examples will serve to further typify the nature of this invention but should not be construed as a limitation in the scope thereof, which scope is defined solely by the appended claims.

EXAMPLE 1

1-(3-Ethoxy-4-methoxyphenyl)-2-methylsutfonylethylamine

To a stirred solution of dimethyl sulfone (3.70 g, 39.4 mmol) in tetrahydrofuran (350 mL), was added n-butyllithium (17.5 mL, 2.5 M, 43.8 mmol) under nitrogen at −78° C. and the mixture was stirred at 78° C. for 25 min. To a stirred solution of 3-ethoxy-4-methoxybenzaldehyde (7.10 g, 39.4 mmol) in tetrahydrofuran (40 mL) under nitrogen in a separate flask at 0° C. was added lithium hexamethyldisilazide (43.0 mL, 1.0 M, 43.0 mmol) in hexane. After 15 min, boron trifluoride etherate (10.0 mL, 78.9 mmol) was added to the resulting mixture at 0° C. After 5 min, this solution was added to the −78° C. sulfone solution via syringe. The solution was allowed to warm to room temperature over one hour. The resulting mixture was then quenched with potassium carbonate (32 g) and water (200 mL). The mixture was stirred for 30 min and the organic layer was separated. The aqueous layer was extracted with ethyl acetate (3×200 mL). The combined organic layers were washed with water (50 mL), brine (50 mL), and then dried over magnesium sulfate. The solvent was removed in vacuo and the resulting solid stirred with ether (100 mL) and 4 N hydrochloric acid (100 mL) for 15 min. The aqueous layer was separated and the organic layer extracted with 4 N hydrochloric acid (30 mL). The combined aqueous layers were washed with ether (50 mL), stirred, and cooled in an ice bath and the pH adjusted to 14 with sodium hydroxide (5 N). This solution was extracted with ethyl acetate (3×100 mL) and the combined organic layers were washed with brine (50 mL) and dried over sodium carbonate and sodium sulfate. Removal of solvent in vacuo gave an oil which was stirred with ether (20 mL) for 20 min to give a suspension. The suspension was filtered and the solid was washed with ether (20 mL) and then dried in a vacuum oven to yield 1-(3-ethoxy-4-methoxyphenyl)-2-methylsulfonylethylamine as an off-white solid (4.17 g, 39%): mp, 116.5–117.0° C.; $^1$H NMR (CDCl$_3$) δ 1.47 (t, J=7 Hz, 3H, CH$_3$), 1.92 (br s 2H, NH$_2$), 2.91 (s, 3H, SO$_2$CH$_3$), 3.19 (dd, J=3.5, 14 Hz, 1H, CHH), 3.36 (dd, J=9.3, 14 Hz 1H, CHH), 3.87 (s, 3H, CH$_3$), 4.10 (q, J=7 Hz, 2H, CH$_2$), 4.60 (dd, J=3.5, 9 Hz, 1H, CH), 6.83–6.93 (m, 3H, Ar); $^{13}$C NMR (CDCl$_3$) δ 14.75, 42.42, 50.94, 55.99, 63.18, 64.44, 110.71, 111.67, 118.21, 135.55, 148.72, 149.09; Anal Calcd for C$_{12}$H$_{19}$NO$_4$S: C, 52.73; H, 7.01; N, 5.12. Found: C, 52.82; H, 6.69; N, 4.99.

EXAMPLE 2

1-(3-Ethoxy-4-methoxyphenyl)-2-(N,N-dimethylaminosulfonyl)ethylamine 1-(3-Ethoxy-4-methoxyphenyl)-2-(N,N-dimethylaminosulfonyl)ethylamine was prepared by a procedure analogous to that of Example 1 from N,N-dimethyl methanesulfonamide (685 mg, 5.56 mmol) and n-butyllithium (2.5 mL, 2.5 M, 6.3 mmol) in tetrahydrofuran (90 mL), and 3-ethoxy-4-methoxybenzaldehyde (1.0 g, 5.5 mmol), lithium hexamethyldisilazide (4.7 mL, 1.3 M, 6.1 mmol) and boron trifluoride etherate (1.4 mL, 11 mmol) in tetrahydrofuran (5 mL). The product was obtained as a white solid (360 mg, 21% yield): mp, 82.0–83.0° C.; $^1$H NMR (CDCl$_3$); δ 1.48 (t, J=7.5 Hz, 3H, CH$_3$), 1.91 (br s, 2H, NH$_2$), 2.88 (s, 6H, N(CH$_3$)$_2$), 3.05 (dd, J=3.0, 13.5 Hz, 1H, CHH), 3.12 (dd, J=9.2, 13.5 Hz, 1H, CHH), 3.88 (s, 3H, CH$_3$), 4.12 (q, J=7.0 Hz, 2H, CH$_2$), 4.61 (dd, J=2.9, 9.2 Hz, 1H, NCH), 6.83–6.99 (m, 3H, Ar); $^{13}$C NMR (CDCl$_3$) δ

14.81; 37.42, 51.02, 56.03, 64.41, 110.74, 111.55, 118.35, 135.97, 148.64, 148.96; Anal Calcd for $C_{13}H_{22}NO_4S$: C, 51.64; H, 7.33; N, 9.26. Found: C, 51, 41; H, 7.11; N, 9.10.

EXAMPLE 3

2-[1-(3-Ethoxy-4-methoxyphenyl)-2-methylsulfonylethyl]isoindolin-1-one

A stirred mixture 1-(3-ethoxy-4-methoxyphenyl)-2-methylsulfonylethylamine (100 mg, 0.37 mmol) and 1,2-phthalic dicarboxaldehyde (49 mg, 0.37 mmol) in acetic acid (2 mL) was heated to reflux for 15 min. Removal of solvent in vacuo and chromatography gave an oil which was stirred with ether (2 mL). The resulting suspension was filtered to yield 2-[1-(3-ethoxy-4-methoxyphenyl)-2-methylsulfonylethyl]isoindolin-1-one as a light yellow solid (100 mg, 70% yield): mp, 130.0–134.0° C.; $^1$H NMR (CDCl$_3$) δ 1.45 (t, J s=7 Hz, 3H, CH$_3$), 2.96 (s, 3H, CH$_3$), 3.70 (dd, J=4.5, 14.7, Hz, 1H, CHH), 3.86 (s, 3H, CH$_3$), 4.07 (q, J=6.9 Hz, 2H, CH$_2$), 4.25 (d, J=16.5 Hz, 1H, CHH), 4.31 (dd, J=10.3, 14.5 Hz, 1H, CHH), 4.46 (d, J=16 HZ, 1H, CHH), 5.71 (dd, J=4.5, 10.3 Hz, 1H, NCH), 6.84–7.01 (m, 3H, Ar), 7.38–7.56 (m, 3H, Ar), 7.85 (d, J=6.9 Hz, 1H, Ar); $^{13}$C NMR (CDCl$_3$) δ 14.65, 41.33, 46.27, 52.33, 55.95, 56.00, 65.56, 111.45, 112.28, 119.30, 122.85, 123.85, 128.13, 129.89, 131.80, 132.27, 141.26, 148.88, 149.62, 169.09; Anal Calcd for $C_{20}H_{23}NO_5S$: C, 61.68; H, 5.95; N, 3.60. Found: C, 61.68, H, 6.06; N, 3.62.

EXAMPLE 4

2-[1-(3-Ethoxy-4-methoxyphenyl)-2-(N,N-dimethylaminosulfonyl)ethyl]isoindolin-1-one 2-[1-(3-Ethoxy-4-methoxyphenyl)-2-(N,N-dimethylaminosulfonyl)ethyl]isoindolin-1-one was prepared by the procedure of Example 3 from 1-(3-ethoxy-4-methoxyphenyl)-2-(N,N-dimethylaminosulfonyl)ethylamine (150 mg, 0.49 mmol) and 1,2-phthalic dicarboxaldehyde (67 mg, 0.49 mmol) in acetic acid (2 mL). The product was obtained as a solid (142 mg, 69% yield): mp, 165.0–167.0° C.; $^1$H NMR (CDCl$_3$) δ 1.45 (t, J=7 Hz, 3H, CH$_3$), 2.86 (s, 6H, N(CH$_3$)$_2$), 3.58 (dd, J=4.7, 14.4 Hz, 1H, CHH), 3.86 (s, 3H, CH$_3$), 4.08 (q, J=7 Hz, 2H, CH$_2$), 4.30 (d, J=16.5 Hz, 1H, NCHH), 4.33 (dd, J=9, 14.4 Hz, 1H, CHH), 4.49 (d, J=16.5 Hz, 1H, NCHH), 5.60 (dd, J=4.7, 9.5 Hz, 1H, NCH), 6.83 (d, J=8.3 Hz, 1H, Ar), 6.98 (dd, J=2, 8.3 Hz, 1H, Ar), 7.06 (d, J=2 Hz, 1H, Ar), 7.37–7.56 (m, 3H, Ar), 7.84 (d, J=7 Hz, 1H, Ar), $^{13}$C NMR (CDCl$_3$) δ 14.69, 37.31, 48.64, 49.73, 52.91, 52.95, 64.54, 111.31, 112.46, 119.29, 122.76, 123.72, 128.03, 130.67, 131.55, 132.75, 141.26, 148.73, 149.39, 168.63; Anal Calcd for $C_{21}H_{26}NO_5S$: C, 60.27; H, 6.26; N, 6.69. Found: C, 60.04; H, 6,10: N, 6.62.

EXAMPLE 5

2-[1-(3-Ethoxy-4-methoxyphenyl)-2-methylsulfonylethyl]isoindoline-1,3-dione A mixture of 1-(3-ethoxy-4-methoxyphenyl)-2-methylsulfonylethylamine (200 mg, 0.73 mmol) and sodium hydrogen carbonate (80 mg, 0.95 mmol) in acetonitrile and water (2 mL each) was stirred under nitrogen at room temperature for 2 minutes. To the resulting solution was added N-ethoxycarbonylphthalimide (170 mg, 0.78 mmol). After 17 hours, the resulting solution was stirred with hydrochloric acid (2 mL, 4 N), and water (30 mL) at room temperature for 30 minutes. The resulting suspension was filtered and the solid was washed with water (2×25 mL), and then dried in a vacuum oven overnight (60° C.,<1 torr) to yield 2-[1-(3-ethoxy-4-methoxyphenyl)-2-methylsulfonylethyl]isoindoline-1,3dione as a solid (206 mg, 70% yield): mp, 151.0–152.0° C.; $^1$H NMR (CDCl$_3$); δ 1.46 (t, J=6.9 Hz, 3H, CH$_3$), 2.84 (s, 3H, CH$_3$), 3.78 (dd, J=4.8, 14.4 Hz, I H, CHH), 3.84 (s, 3H, CH$_3$), 4.10 (q, J=7 Hz, 2H, CH$_2$), 4.54 (dd, J=10.1, 14.4 Hz, 1H, CHH), 5.90 (dd, J=4.8, 1 0.1 Hz, 1H, NCH), 6.83 (d, J=8.5 Hz, 1H, Ar), 7.11–7.15 (m, 2H, Ar), 7.67–7.73 (m, 2H, Ar), 7.80–7.84 (m, 2H, Ar); $^{13}$C NMR (CDCl$_3$) δ 14.63, 41.49, 48.84, 54.82, 55.89, 64.45, 111.43, 112.50, 120.43, 123.51, 129.56, 131.58, 134.17, 148.57, 149.63, 167.80; Anal Calcd for $C_{20}H_{21}NO_6S$: C, 59.54; H, 5.25; N, 3.47. Found: C, 59.66; H, 5.28; N, 3.29.

EXAMPLE 6

2-[1-(3-Ethoxy-4-methoxyphenyl)-2-methylsuyonylethyl]-5-nitro-isoindoline-1,3-dione A stirred mixture of 1-(3-ethoxy-4-methoxyphenyl)-2-methylsulfonylethylamine (1.0 g, 3.7 mmol) and 4-nitrophthalic anhydride (706 mg, 3.66 mmol) was heated to melt for 6 min. The mixture was allowed to cool to room temperature. Chromatography of the resulting oil gave 2-[1-(3-ethoxy-4-methoxyphenyl)-2-methylsulfonylethyl]-5-nitro-isoindoline-1,3-dione as a solid (1.42 g, 87% yield): mp, 255.0–256.0° C.; $^1$H NMR (CDCl$_3$); δ 1.47 (t, J=7 Hz, 3H, CH$_3$), 2.91 (s, 3H, CH$_3$), 3.71 (dd, J=4.2, 14.3 Hz, 1H, CHH), 3.85 (2, 3H, CH$_3$), 4.10 (q, J=7 Hz, 2H, CH$_2$), 4.59 (dd, J=11.1, 14.1, Hz, 1H, CHH), 5.94 (dd, J=4.1, 10.9 Hz, 1H, NCH), 6.82–6.86 (m, 2H, Ar), 7.09–7.14 (m, 2H, Ar), 8.01–8.04 (m, 1H, Ar), 8.56–8.65 (m, 1H, Ar), $^{13}$C NMR (CDCl$_3$) δ 14.67, 41.61, 49.16, 53.99, 55.96, 64.54, 111.48, 112.39, 118.98, 120.48, 124.79, 128.73, 129.39, 133.06, 136.03, 148.71, 149.92, 151.79, 165.56, 165.74; Anal Calcd for $C_{20}H_{20}NO_8S$: C, 53.57; H, 4.50; N, 6.23. Found: C, 53.59; H, 4.58; N, 5.88.

EXAMPLE 7

2-[1-(3-Ethoxy-4-methoxyphenyl)-2-methylsulfonylethyl]-5-aminoisoindoline-1,3-dione A mixture of 2-[1-(3-ethoxy-4-methoxyphenyl)-2-methylsulfonylethyl]-5-nitro-isoindoline-1,3-dione (600 mg, 1.33 mmol) and Pd/C (100 mg, 10%) in ethyl acetate (40 mL) was shaken under hydrogen (50 psi) for 7 h in Parr type shaker. The mixture was filtered through a pad of celite, and the pad was washed with ethyl acetate (50 mL). The filtrate was concentrated in vacuo to give a solid. The solid was stirred in a mixture of methylene chloride (2 mL) and hexane (10 mL). The resulting suspension was filtered to give 2-[1-(3-ethoxy-4-methoxyphenyl)-2-methylsulfonylethyl]-5-aminoisoindoline-1,3-dione as a yellow solid (500 mg, 90% yield): mp, 224.5–227.0° C.; $^1$H NMR (DMSO-d$_6$); δ 1.32 (t, J=6.8 Hz, 3H, CH$_3$), 2.99 (s, 3H, CH3), 3.73 (s, 3H, CH$_3$), 3.73 (s, 3H, CH$_3$), 4.00 (q, J=7 Hz, 2H, CH$_2$), 4.03–4.09 (m, 1H, CHH), 4.34 (dd, J=10.3, 14.2 HZ, 1H, CHH), 5.70 (dd, J=3.7, 10.2 Hz, 1H, NCH), 6.52 (br, s, 2H, NH$_2$), 6.79–6.81 (m, 1H, Ar), 6.92 (br s, 3H, Ar), 7.06 (br s, 1H, Ar), 7.48 (d, J=8.2 Hz, 1H, Ar); $^{13}$C NMR (DMSO-d$_6$) δ 14.64, 40.99, 46.99, 53.34, 55.46, 63.80, 106.99, 111.78, 112.31, 116.12, 116.80, 118.61, 125.12, 130.33, 134.11, 147.80, 148.74, 155.13, 167.39, 167.86; Anal Calcd for $C_{20}H_{22}NO_6S$: 57.41; H, 5.30; N, 6.69. Found: C, 57.03; H, 5.40; N, 6.33.

EXAMPLE 8

2-[1-(3-Ethoxy-4-methoxyphenyl)-2-methylsulfonylethyl]-4-nitroisoindoline-1,3-dione A stirred solution 1-(3-ethoxy-4-methoxyphenyl)-2-methylsulfonylethylamine (640 mg, 2.34 mmol) and 3-nitrophthalic anhydride (460 mg, 2.34 mmol) in acetic acid (10 mL) was heated at reflux for 15 h. The solvent was removed in vacuo to yield an oil. Chromatography of the resulting oil yielded 2-[1-(3-ethoxy-4-methoxyphenyl)-2-methylsulfonylethyl]-4-nitroisoindoline-1,3-dione as a yellow solid (850 mg, 81% yield): mp, 110.0–114.0° C.; $^1$H NMR (CDCl$_3$); δ 1.47 (t, J=7.0 Hz, 3H, CH$_3$), 2.90 (s, 3H, CH$_3$), 3.71 (dd, J=4.3, 14.4 Hz, 1H, CHH), 3.85 (s, 3H, CH$_3$), 4.10 (q, J=7.0 Hz, 2H, CH$_2$), 4.58 (dd, J=10.7, 14.4 Hz, 1H, CHH), 5.93 (dd, J=4.2, 10.7 Hz, 1H, NCH), 6.84 (d, J=8.8 Hz, 1H, Ar), 7.11–7.15 (m, 2H, Ar), 7.89 (t, J=7.8 Hz, 1H, Ar), 8.08–8.13 (m, 2H, Ar); $^{13}$C NMR (CDCl$_3$) δ 14.67, 41.56, 49.19, 53.97, 55.96, 64.56, 111.52, 112.51, 120.62, 123.44, 127.35, 128.65, 128.84, 133.73, 135.48, 145.24, 148.68, 149.92, 162.53, 165.33; Anal Calcd for C$_{20}$H$_{20}$NO$_8$S: C, 53.57; H, 4.50; N, 6.23. Found: C, 53.54; H, 4.28; N, 6.32

EXAMPLE 9

2-[1-(3-Ethoxy-4-methoxyphenyl)-2-methylsutfonylethyl]-4-aminoisoindoline-1,3-dione A mixture of 2-[1-(3-ethoxy-4-methoxyphenyl)-2-methylsulfonylethyl]-4-nitroisoindoline-1,3 1,3-dione (710 mg, 1.58 mmol) and Pd/C (200 mg) in ethyl acetate/acetone (40 mL each) was shaken under H$_2$ (50 psi) in a Parr Type Shaker for 5 hours. The suspension was filtered through a pad of magnesium sulfate. The filtrate was concentrated in vacuo to give an oil. The oil was stirred with ethyl acetate (a mL), hexane (2 mL) and ether (2 ML) for 1 h. The resulting suspension was filtered and the solid was dried in a vacuum oven to give 2-[1-(3-ethoxy-4-methoxyphenyl)-2-methylsulfonylethyl]-4-aminoisoindoline-1,3-dione as a yellow solid (550 mg, 83% yield): mp, 135.0–137.5° C.; $^1$H NMR (DMSO-d$_6$); δ 1.32 (t, J=6.9 Hz, 3H, CH$_3$), 3.00 (s, 3H, CH$_3$), 3.73 (s, 3H, CH$_3$), 4.00 (q, J=6.9 Hz, 2H, CH$_2$), 4.08 (dd, J=4.2, 14.5 Hz, 1H, CHH), 4.36 (dd, J=10.8, 14.2 Hz, 1H, CHH), 5.72 (dd, J=4.1, 10.3 Hz, 1H, NCH), 6.51(br s, SH, NH$_2$), 6.89–7.07 (m, 5H, Ar), 7.43 (t, J=7.4, Hz, 1H, Ar); $^{13}$C NMR (CDCl$_3$) δ 14.68, 41.55, 48.62, 55.23, 55.93, 64.48, 110.70, 111.42, 112.52, 112.96, 120.38, 121.30, 129.95, 132.23, 135.37, 145.56, 148.56, 149.56, 168.19, 169.43; Anal Calcd for C$_{20}$H$_{22}$NO$_6$S: C, 57.41; H, 5.30; N, 6.69. Found C, 57.11; H, 5.23; N, 6.43.

EXAMPLE 10

2-[1-(3-Ethoxy-4-methoxyphenyl)-2-methylsulffonylethyl]-4-methylisoindoline-1,3-dione 2-[1-(3-Ethoxy-4-methoxyphenyl)-2-methylsulfonylethyl]-4-methylisoindoline-1,3-dione was prepared by the procedure of Example 8 from 1-(3-ethoxy-4-methoxyphenyl)-2-methylsulfonylethylamine (1.4 g, 5.0 mmol) and 3-methylphthalic anhydride (810 mg, 5.0 mmol) in acetic acid (15 mL) to afford 2-[1-(3-ethoxy-4-methoxyphenyl)-2-methylsulfonylethylamine (1.0 g, 3.7 mmol) and 3-methylphtalic anhydride (590 mg, 3.7 mmol). The product was obtained as a white solid (1.78 g, 85% yield); mp, 143.0–145.0° C.; $^1$H NMR (CDCl$_3$) δ 1.46 (t, J=7.0 Hz, 3H, CH$_3$), 2.67 (s, 3H, CH$_3$), 2.83 (s, 3H, CH$_3$), 3.79 (dd, J=4.8, 14.5 Hz, 1H, CHH), 3.85 (s, CH, CH$_3$), 4.11 (q, J=7.0 Hz, 2H, CH$_2$), 4.54 (dd, J=9.8, 14.5 Hz, 1H, CHH), 5.89 (dd, J=4.8, 9.9 Hz, 1H, NCH), 6.81–6.85 (m, 1H, Ar), 7.65 (d, J=7.5 Hz, 1H, Ar); $^{13}$C NMR (CDCl$_3$) δ 14.65, 17.54, 41.49, 48.63, 54.89, 55.89, 64.44, 111.36, 112.48, 120.44, 121.17, 128.24, 129.69, 132.00, 133.69, 136.63, 138.29, 148.51, 149.55, 167.99, 168.46; Anal Calcd for C$_{21}$H$_{23}$NO$_6$S: C, 60.42; H, 5.55; N, 3.36. Found: C, 60.68; H, 5.40; N, 3.15.

EXAMPLE 11

2-[1-(3-Ethoxy-4-methoxyphenyl)-2-methylsulfonylethyl]-5-methylisoindoline-1,3-dione 2-[1-(3-Ethoxy-4-methoxyphenyl)-2-methylsulfonylethyl]-5-methylisoindoline-1,3-dione was prepared by the procedure of Example 6 from 1-(3-ethoxy-4-methoxyphenyl)-2-methylsulfonylethylamine (1.0 g, 3.7 mmol) and 4-methylphythalic anhydride (590 mg, 3.7 mmol). The product was obtained as a white solid (710 mg, 46% yield): mp, 87.0–89.0° C.; $^1$H NMR (CDCl$_3$) δ 1.45 (t, J–7.0 Hz, 3H, CH$_3$), 2.47 (s, 3H, CH$_3$), 2.84 (s, 3H, CH$_3$), 3.77–3.84 (m, 1H, CHH), 3.84 (s, 3H, CH$_3$), 4.09 (q, J=7.0 Hz, 2H, CH$_2$), 4.54 (dd, J=10.2, 14.4 Hz, 1H, CHH), 5.89 (dd, J=4.7, 10.1 Hz, 1H, NCH), 6.83 (d, J=8.0 Hz, 1H, Ar), 7.09–7.15 (m, 2H, Ar), 7.47 (d, J=7.7 Hz, 1H, Ar), 7.60 (s, 1H, Ar), 7.67 (d, J=7.6 Hz, 1H, Ar); $^{13}$C NMR (CDCl$_3$) δ 14.51, 21.77, 41.31, 48.56, 54.59, 55.73, 64.26, 111.24, 112.31, 120.25, 123.26, 123.86, 128.81, 129.57, 131.79, 134.59, 145.43, 148.34, 149.36, 167.72, 167.87; Anal Calcd for C$_{21}$H$_{23}$NO$_6$S: C, 60.42; H, 5.55; N, 3.36. Found: C, 60.34; H, 5.49; N, 3.21.

EXAMPLE 12

2-[1-(3-Ethoxy-4-methoxyphenyl)-2-methylsulfonylethyl]-4-acetamidoisoindoline-1,3-dione 2-[1-(3-Ethoxy-4-methoxyphenyl)-2-methylsulfonylethyl]-4-acedtamidoisoindoline-1,3-dione was prepared by the procedure of Example 8 from 1-(3-ethoxy-4-methoxyphenyl)-2-methylsulfonylethylamine (1.0 g, 3.7 mmol) and 3-acetamidophthalic anhydride (751 mg, 3.66 mmol) in acetic acid (20 mL). The product was obtained as a yellow solid (1.0 g, 59% yield): mp, 144.0° C.; $^1$H NMR (CDCl$_3$) δ 1.47 (t, J=7.0 Hz, 3H, CH$_3$), 2.26 (s, 3H, CH$_3$), 2.88 (s, 3H, CH$_3$), 3.75 (dd, J=4.4, 14.3 Hz, 1H, CHH), 5.87 (dd, J=4.3, 10.5 Hz, 1H, NCH), 6.82–6.86 (m, 1H, Ar), 7.09–7.11 (m, 2H, Ar), 9.49 (br s, 1H, NH), $^{13}$C NMR (CDCl$_3$) δ 14.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calcd for C$_{22}$H$_{24}$NO$_7$S: C, 57.38; H, 5.25; N, 6.08. Found: C, 57.31; H, 5.34; N, 5.83.

EXAMPLE 13

2-[1-(3-Ethoxy-4-methoxyphenyl)-2-methylsulfonylethyl]-5-acetamidoisoindoline-1,3-dione 2-[1-(3-Ethoxy-4-methoxyphenyl)-2-methylsulfonylethyl]-5-acetamidoisoindoline-1,3-dione was prepared by the procedure of Example 6 from 1-(3-ethoxy-4-methoxyphenyl)-2-methylsulfonylethylamine (1.0 g, 3.7 mmol) and 4-acetamidophthalic anhydride (751 mg, 3.66 mmol). The product was obtained as a yellow solid (330 mg, 20% yield): mp, 215.0–217.0° C.; $^1$H NMR (DMSO-$d_6$) δ 1.32 (t, J=6.9 Hz, 3H, $CH_3$), 2.12 (s, 3H, $CH_3$), 2.99 (s, 3H, $CH_3$), 3.73 (s, 3H, $CH_3$), 4.00 (q, J=7.0 Hz, 2H, $CH_2$), 4.12 (dd, J=4.5, 14.3 Hz, 1H, CHH), 4.35 (dd, J=10.5, 14.2 Hz, 1H, CHH), 5.76 (dd, J=4.5, 10.5 Hz, 1H, NCH), 6.90–6.98 (m, 2H, Ar), 7.08 (br s, 1H, Ar), 7.83–7.84 (m, 2H, Ar), 8.19 (br s, 1H, Ar), 10.95 (br s, 1H, NH); $^{13}$C NMR (DMSO-$d_6$) δ 14.66, 24.22, 41.05, 47.35, 53.07, 55.47, 63.80, 111.74, 112.28, 112.72, 123.34, 124.59, 124.66, 129.74, 132.68, 145.00, 147.85, 148.84, 167.00, 167.28, 169.36; Anal Calcd for $C_{22}H_{24}NO_7S$: C, 57.38; H, 5.25; N, 6.08. Found: C, 57.13; H, 5.18; N, 5.74.

EXAMPLE 14

2-[1-(3-Ethoxy-4-methoxphenyl)-2-methylsutfonylethyl]-4-dimethylaminoisoindoline-1,3-dione 2-[1-(3-Ethoxy-4-methoxyphenyl)-2-methylsulfonylethyl]-4-dimethylaminoisoindoline-1,3-dione was prepared by the procedure of Example 8 from 1-(3-ethoxy-4-methoxyphenyl)-2-methylsulfonylethylamine (572 mg, 2.09 mmol) and 3-dimethylaminophthalic anhydride (400 mg, 2.09 mmol) in acetic acid (20 mL). The product was obtained as a yellow solid (740 mg, 80% yield): mp, 94.0–96.0° C.; $^1$H NMR ($CDCl_3$) δ 1.46 (t, J=7.0 Hz, 3H, $CH_3$), 2.82 (s, 3H, $CH_3$), 3.08 (s, 6H, $CH_3$), 3.76–3.84 (m, 1H, CHH), 3.82 (s, 3H, $CH_3$), 4.11 (q, J=7.0 Hz, 2H, $CH_2$), 4.54 (dd, J=9.9, 14.5 Hz, 1H, CHH), 5.88 (dd, J=4.8, 9.9 Hz, 1H, NCH), 6.81–6.84 (m, 1H, Ar), 7.04–7.15 (m, 3H, Ar), 7.23–7.27 (m, 1H, Ar), 7.48 (dd, J=7.3, 8.3 Hz, 1H, Ar); $^{13}$C NMR ($CDCl_3$) δ 14.68, 41.47, 43.39, 48.74, 55.20, 55.92, 64.43, 111.34, 112.54, 113.78, 114.41, 120.47, 122.09, 129.97, 134.32, 134.81, 148.46, 149.44, 150.42, 167.06, 168.19; Anal Calcd for $C_{22}H_{26}NO_6S$: C, 59.14; H, 5.91; N, 6.27. Found: C, 59.14; H, 5.91; N, 6.10.

EXAMPLE 15

2-[1-(3-Ethoxy-4-methoxyphenyl)-2-methylsulfonylethyl]-5-dimethylaminoisoindoline-1,3-dione 2-[1-(3-Ethoxy-4-methoxyphenyl)-2-methylsulfonylethyl]-5-dimethylaminoisoindoline-1,3-dione was prepared by the procedure of Example 8 from 1-(3-ethoxy-4-methoxyphenyl)-2-methylsulfonylethylamine (572 mg, 2.09 mmol) and 4-dimethylaminophthalic anhydride (400 mg, 2.09 mmol) in acetic acid (20 mL). The product was obtained as a yellow solid (200 mg, 21% yield): mp, 161.5–163.50° C.; $^1$H NMR (DMSO-$d_6$) δ 1.46 (t, J=6.9 Hz, 3H, $CH_3$), 2.79 (s, 3H, $CH_3$), 3.09 (s, 6H, $CH_3$), 3.78–3.85 (m, 1H, CHH), 3.85 (s, 3H, $CH_3$), 4.11 (q, J=7.0 Hz, 2H, $CH_2$), 4.51 (dd, J=9.7, 14.6 Hz, 1H, NCHH), 5.85 (dd, J=5.1, 9.6 Hz, AH, NCH), 6.75–6.84 (m, 2H, Ar), 7.03 (d, J=2.3 Hz, 1H, Ar), 7.10–7.16 (m, 2H, Ar), 7.61 (d, J=8.5 Hz, 1H, Ar); $^{13}$C NMR (DMSO-$d_6$) δ 14.65, 40.40, 41.43, 48.83, 55.42, 55.89, 64.38, 105.80, 111.29, 112.43, 114.86, 116.90, 120.38, 125.11, 130.14, 134.27, 148.46, 149.38, 154.44, 168.14, 168.67; Anal Calcd for $C_{22}H_{26}NO_6S+0.2 H_2O$: C, 58.70; H, 5.91; N, 6.22. Found: C, 58.70; H, 5.93; N, 5.84.

EXAMPLE 16

2-[1-(3-Ethoxy-4-methoxyphenyl)-2-methylsulfonylethyl]benzo[e]isoindoline-1,3-dione 2-[1-(3-Ethoxy-4-methoxyphenyl)-2-methylsulfonylethyl]benzo[e]isoindoline-1,3-dione was prepared by the procedure of Example 8 from 1-(3-ethoxy-4-methoxyphenyl)-2-methylsulfonylethylamine (1.31 g, 4.79 mmol) and 1,2-naphthalic anhydride (950 mg, 4.79 mmol) in acetic acid (15 mL). The product was obtained as a yellow solid (1.65 g, 76% yield): mp, 158.0–159.5° C.; $^1$H NMR (DMSO-$d_6$) δ 1.33 (t, J=6.9 Hz, 3H, $CH_3$), 3.03 (s, 3H, $CH_3$), 3.73 (s, 3H, $CH_3$), 4.03 (q, J=6.9 Hz, 2H, $CH_2$), 4.18 (dd, J=4.3, 14.3 Hz, 1H, CHH), 4.41 (dd, J=10.7, 14.4 Hz, 1H, CHH), 5.86 (dd, J=4.2, 10.3 Hz, 1H, NCH), 6.83–6.96 (m, 1H, Ar), 7.03–7.07 (m, 1H, Ar), 7.15 (br s, 1H, Ar), 7.70–7.9 (m, 3H, Ar), 8.15 (d, J=8.0 Hz, 1H, Ar), 8.39 (d, J=8.3 Hz, 1H, Ar), 8.76 (d, J=8.2 Hz, 1H, Ar); $^{13}$C NMR (DMSO-$d_6$) δ 19.86, 46.29, 52.48, 58.35, 60.67, 69.03, 116.96, 117.57, 123.65, 124.97, 128.97, 131.40, 132.30, 134.15, 134.36, 134.94, 135.16, 135.89, 140.85, 11.42, 153.09, 154.06, 173.09, 173.82; Anal Calcd for $C_{24}H_{23}NO_6S$: C, 63.56; H, 5.11; N, 3.09. Found: C, 63.33; H, 5.06; N, 2.95.

EXAMPLE 17

2-[1-(3-Ethoxy-4-methoxyphenyl)-2-methylsulfonylethyl]-4-methoxyisoindoline-1,3-dione 2-[1-(3-Ethoxy-4-methoxyphenyl)-2-methylsulfonylethyl]-4-methoxyisoindoline-1,3-dione was prepared by the procedure of Example 8 from 1-(3-ethoxy-4-methoxyphenyl)-2-methylsulfonylethylamine (580 mg, 2.12 mmol) and 3-methoxyphthalic anhydride (380 mg, 2.13 mmol) in acetic acid (15 mL). The product was obtained as a white solid (620 mg, 67% yield): mp, 162.5–164.5° C.; $^1$H NMR ($CDCl_3$) δ 1.45 (t, J=6.9 Hz, 3H, $CH_3$), 2.85 (s, 3H, $CH_3$), 3.78 (dd, J=4.7, 10.5 Hz, 1H, CHH), 3.84 (s, 3H, $CH_3$), 3.99 (s, 3H, $CH_3$), 4.09 (q, J=6.9 Hz, 2H, $CH_2$), 4.54 (dd, J=10.3, 14.4 Hz, 1H, CHH), 5.87 (dd, J=4.6, 10.7 Hz, 1H, NCH), 6.80–6.83 (m, 1H, Ar), 7.10–7.18 (m, 3H, Ar), 7.38 (d, J=7.3 Hz, 1H, Ar), 7.63 (dd, J=7.5, 8.2 Hz, 1H, Ar); $^{13}$C NMR ($CDCl_3$) δ 14.57, 41.32, 48.52, 54.62, 55.82, 56.19, 64.38, 111.35, 112.52, 115.56, 116.75, 117.58, 120.40, 129.58, 133.59, 136.30, 148.41, 149.46, 156.74, 166.43, 167.35; Anal Calcd for $C_{21}H_{23}NO_7S$: C, 58.19; H, 5.35; N, 3.23. Found: C, 58.05; H, 5.35; N, 3.24.

EXAMPLE 18

1-(3-Cyclopentyloxy-4-methoxyphenyl)-2-methylsutfonylethylamine 1-(3-Cyclopentyloxy-4-methoxyphenyl)-2-methylsulfonylethylamine was prepared by the procedure of Example 1 from dimethyl sulfone (23.14 g, 246.1 mmol) and n-butyllithium (100 mL, 2.5 M, 250 mmol) in tetrahydrofuran (700 mL), and 3-cyclopentyloxy-4-methoxybenzaldehyde (49.50 g, 224.7 mmol), lithium hexamethyldisilazide (246 mL, 1.0 M, 246 mmol) and boron trifluoride etherate (58 mL, 458 mmol) in tetrahydrofuran (200 mL). The product was obtained as a white solid (26.53 g, 38% yield): mp, 155.0–158.0° C.; $^1$H NMR ($CDCl_3$); δ 1.60–1.65 & 1.81–1.96 (m, 8H, $C_5H_8$), 2.91 (s, 3H, $CH_3$), 3.22 (dd, J=3.7, 14.2 Hz, 1H, CHH), 3.33 (dd, J=9.1, 14.1 Hz, 1H, CHH), 3.84 (s, 3H, $CH_3$), 4.58 (q, J=3.7, 9.0 Hz, 1H, NCH), 4.77–4.82 (m, 1H, OCH), 6.82–6.92 (m, 3H, Ar); $^{13}$C NMR ($CDCl_3$) δ 23.95, 32.76, 42.42, 50.96, 56.11, 63.22, 80.56, 112.21, 113.00, 118.18, 135.53, 148.09, 149.89; Anal Calcd for $C_{15}H_{23}NO_4S$: C, 57.49; H, 7.40; N, 4.47. Found: C, 58.14; H, 7.42; N, 4.37.

EXAMPLE 19

2-[1-(3-Cyclopentyloxy-4-methoxyphenyl)-2-methylsulfonylethyl]isoindoline-1,3-dione 2-[1-(3-Cyclopentyloxy-4-methoxyphenyl)-2-methylsulfonylethyl]isoindoline-1,3-dione was prepared by the procedure of Example 5 from 1-(3-cyclopentyloxy-4-methoxyphenyl)-2-methylsulfonylethylamine (1.0 g, 3.2 mmol), sodium hydrogen carbonate (281 mg, 3.34 mmol) and N-ethoxycarbonyl phthalimide (732 mg, 3.3 mmol) in acetonitrile and water (4 mL each). The product was obtained as a white solid (314 mg, 22% yield): mp, 173.0–175.0° C.; $^1$H NMR (CDCl$_3$); δ 1.61–2.05 (m, 8H, C$_5$H$_8$), 2.84 (s, 3H, CH$_3$), 3.80 (dd, J=4.9, 14.4 Hz, 1H, CHH), 3.83 (s, 3H, CH$_3$), 4.54 (dd, J=9.9, 14.4 Hz, 1H, CHH), 4.77–4.82 (m, 1H, OCH), 5.90 (dd, J=4.9, 9.9 Hz, 1H, NCH), 6.82 (d, J=8.3 Hz, 1H, Ar), 7.09–7.17 (m, 2H, Ar), 7.69–7.75 (m, 2H, Ar), 7.81–7.86 (m, 2H, Ar); $^{13}$C NMR (CDCl$_3$) δ 24.08, 32.77, 41.53, 48.98, 54.99, 56.03, 80.59, 111.92, 114.57, 120.37, 123.55, 129.55, 131.67, 134.20, 148.02, 150.38, 167.82; Anal Calcd for C$_{23}$H$_{25}$NO$_6$S+0.1 CH$_2$Cl$_2$: C, 61.38; H, 5,62; N, 3.10. Found: C, 61.05; H, 5.60; N, 2.96.

EXAMPLE 20

2-[1-(3-Cyclopentyloxy-4-methoxyphenyl)-2-methylsulfonylethyl]-4-dimethylaminoisoindoline-1,3-dione 2-[1-(3-Cyclopentyloxy-4-methoxyphenyl)-2-methylsulfonylethyl]-4-dimethylaminoisoindoline-1,3-dione was prepared by the procedure of Example 8 from 1-(3-Cyclopentyloxy-4-methoxyphenyl)-2-methylsulfonylethylamine (1.0 g, 3.18 mmol) and 3-dimethylaminophthalic anhydride (608 mg, 3.18 mmol) in acetic acid (10 mL). The product was obtained as a yellow solid (780 mg, 50% yield): mp, 192.0–194.0° C.; $^1$H NMR (CDCl$_3$) δ 1.61–1.64 & 1.82–2.00 (2 m's, 8H, C$_5$H$_8$), 2.79 (s, 3H, CH$_3$), 3.08 (s, 6H, CH$_3$), 3.81 (s, 3H, CH$_3$), 3.82 (dd, J=5.5, 14.5 Hz, 1H, CHH), 4.52 (dd, J=9.8, 14.5 Hz, 1H, CHH), 4.75–4.81 (m, 1H, OCH), 5.87 (dd, J=5.0, 9.7 Hz, 1H, NCH), 6.80 (d, J=8.3 Hz, 1H, Ar), 7.03–7.26 (m, 3H, Ar), 7.47 (dd, J=7.3, 8.4 Hz, 1H, Ar); $^{13}$C NMR (CDCl$_3$) δ 24.05, 32.75, 41.47, 43.37, 48.84, 55.36, 56.02, 80.55, 111.88, 113.74, 114.46, 114.71, 120.41, 122.04, 129.88, 134.39, 134.77, 147.91, 150.22, 150.39, 167.05, 168.13; Anal Calcd for C$_{25}$H$_{30}$N$_2$O$_6$S: C, 61.71; H, 6.21; N, 5.76. Found: C, 61.58; H, 6.06; N, 5.53.

EXAMPLE 21

Tablets, each containing 50 mg of 1-oxo-2-(2,6-dioxo-3-methylpiperidin-3-yl)-4,5,6,7 tetrafluoroisoindoline, can be prepared in the following manner:

| Constituents (for 1000 tablets) | | |
|---|---|---|
| 2-[1-(3-ethoxy-4-methoxy-phenyl)-2-methylsulfonyl-ethyl]isoindolin-1-one | 50.0 | g |
| lactose | 50.7 | g |
| wheat starch | 7.5 | g |
| polyethylene glycol 6000 | 5.0 | g |
| talc | 5.0 | g |
| magnesium stearate | 1.8 | g |
| demineralized water | q.s. | |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 22

Tablets, each containing 100 mg of 2-[1-(3-ethoxy-4-methoxyphenyl)-2-(N,N-dimethylaminosulfonyl)ethyl] isoindolin-1-one, can be prepared in the following manner:

| Constituents (for 1000 tablets) | | |
|---|---|---|
| 2-[1-(3-ethoxy-4-methoxy-phenyl)-2-(N,N-dimethyl-aminosulfonyl)ethyl]-isoindolin-1-one | 100.0 | g |
| lactose | 100.0 | g |
| wheat starch | 47.0 | g |
| magnesium stearate | 3.0 | g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 23

Tablets for chewing, each containing 75 mg of 2-[1-(3-ethoxy-4-methoxyphenyl)-2-methylsulfonylethyl] isoindoline-1,3-dione, can be prepared in the following manner:

| Constituents (for 1000 tablets) | | |
|---|---|---|
| 2-[1-(3-ethoxy-4-methoxy-phenyl)-2-methylsulfonyl-ethyl]isoindoline-1,3-dione | 75.0 | g |
| mannitol | 230.0 | g |
| lactose | 150.0 | g |
| talc | 21.0 | g |
| glycine | 12.5 | g |
| stearic acid | 10.0 | g |
| saccharin | 1.5 | g |
| 5% gelatin solution | q.s. | |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 2-[1-(3-Ethoxy-4-methoxyphenyl)-2-methylsulfonylethyl] isoindoline-1,3-dione, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 24

Tablets, each containing 10 mg of 2-(2,6-dioxoethylpiperidin-3-yl)-4-aminophthalimide, can be prepared in the following manner:

| Constituents (for 1000 tablets) | | |
|---|---|---|
| 2-[1-(3-ethoxy-4-methoxy-phenyl)-2-methylsulfonyl-ethyl]-5-nitro-isoindoline-1,3-dione | 10.0 | g |
| lactose | 328.5 | g |
| corn starch | 17.5 | g |
| polyethylene glycol 6000 | 5.0 | g |
| talc | 25.0 | g |
| magnesium stearate | 4.0 | g |
| demineralized water | q.s. | |

The solid ingredients are first forced through a sieve of 0.6 mm mesh width. Then the active ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 25

Gelatin dry-filled capsules, each containing 100 mg of 2-[1-(3-ethoxy-4-methoxyphenyl)-2-methylsulfonylethyl]-4-aminoisoindoline-1,3-dione, can be prepared in the following manner:

| Constituents (for 1000 capsules) | | |
|---|---|---|
| 2-[1-(3-ethoxy-4-methoxy-phenyl)-2-methylsulfonyl-ethyl]-4-aminoisoindoline-1,3-dione | 100.0 | g |
| microcrystalline cellulose | 30.0 | g |
| sodium lauryl sulfate | 2.0 | g |
| magnesium stearate | 8.0 | g |

The sodium lauryl sulfate is sieved into the 2-[1-(3-ethoxy-4-methoxyphenyl)-2-methylsulfonylethyl]-4-aminoisoindoline-1,3-dione through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 26

A 0.2% injection or infusion solution can be prepared, for example, in the following manner:

| 2-[1-(3-ethoxy-4-methoxy-phenyl)-2-methylsulfonyl-ethyl]-4-aminoisoindoline 1,3-dione hydrochloride | 5.0 | g |
|---|---|---|
| sodium chloride | 22.5 | g |
| phosphate buffer pH 7.4 | 300.0 | g |
| demineralized water | to 2500.0 | mL |

2-[1-(3-Ethoxy-4-methoxyphenyl)-2-methylsulfonylethyl]-4-aminoisoindoline-1,3-dioxoisoindoline as the hydrochloride is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of active ingredient).

What is claimed is:

1. A sulfone selected from the group consisting of
   (a) a compound of the formula:

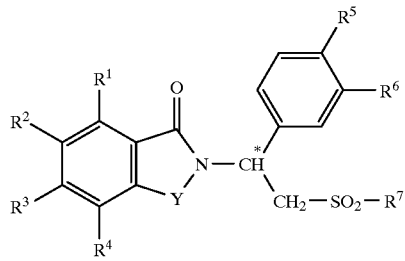

in which:
   the carbon atom designated * constitutes a center of chirality;
   Y is C=O, CH$_2$, or CH$_2$C=O;
   each of R$^1$, R$^2$, R$^3$, and R$^4$, independently of the others, is hydrogen, halo, alkyl of 1 to 4 carbon atoms, alkoxy of 1 to 4 carbon atoms, nitro, cyano, hydroxy, or —NR$^8$R$^9$; or any two of R$^1$, R$^2$, R$^3$, and R$^4$ on adjacent carbon atoms, together with the depicted phenylene ring are naphthylidene
   each of R$^5$ and R$^6$, independently of the other, is hydrogen, alkyl of 1 to 4 carbon atoms, alkoxy of 1 to 4 carbon atoms, cyano, or cycloalkoxy of up to 18 carbon atoms;
   R$^7$ is hydroxy, alkyl of 1 to 8 carbon atoms, phenyl, benzyl, or NR$^8$R$^9$; each of R$^8$ and R$^9$ taken independently of the other is hydrogen, alkyl of 1 to 8 carbon atoms, phenyl, or benzyl, or one of R$^8$ and R$^9$ is hydrogen and the other is —COR$^{10}$, or —SO$_2$R$^{10}$, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—;
   each of R$^{8'}$ and R$^{9'}$ taken independently of the other is hydrogen, alkyl of 1 to 8 carbon atoms, phenyl, or benzyl, or one of R$^{8'}$ and R$^{9'}$ is hydrogen and the other is —COR$^{10'}$, or —SO$_2$R$^{10'}$, or R$^{8'}$ and R$^{9'}$ taken together are tetramethylene, pentamethylene, hexamethylene, or —CH$_2$CH$_2$X$^2$CH$_2$CH$_2$— in which X$^2$ is —O—, —S— or —NH—;
   R$^{10}$ is hydrogen, alkyl of 1 to 8 carbon atoms, or phenyl; and
   R$^{10'}$ is hydrogen, alkyl of 1 to 8 carbon atoms, or phenyl; and
   (b) the acid addition salts of said compounds which contain a nitrogen atom susceptible of protonation.

2. A sulfone according to claim 1 wherein in said compound, Y is C=O.

3. A sulfone according to claim 1 wherein in said compound, Y is $CH_2$.

4. A sulfone according to claim 1 wherein in said compound, each of $R^1$, $R^2$, $R^3$, and $R^4$, independently of the others, is hydrogen, halo, methyl, ethyl, methoxy, ethoxy, nitro, cyano, hydroxy, or —$NR^8R^9$ in which each of $R^8$ and $R^9$ taken independently of the other is hydrogen or methyl or one of $R^{8'}$ and $R^{9'}$ is hydrogen and the other is —$COCH_3$.

5. A sulfone according to claim 1 wherein in said compound, one of $R^1$, $R^2$, $R^3$, and $R^4$ is —$NH_2$ and the remaining of $R^1$, $R^2$, $R^3$ and $R^4$ are hydrogen.

6. A sulfone according to claim 1 wherein in said compound, one of $R^1$, $R^2$, $R^3$, and $R^4$ is —$NHCOCH_3$ and the remaining of $R^1$, $R^2$, $R^3$, and $R^4$ are hydrogen.

7. A sulfone according to claim 1 wherein in said compound, one of $R^1$, $R^2$, $R^3$, and $R^4$ is methyl or ethyl and the remaining of $R^1$, $R^2$, $R^3$, and $R^4$ are hydrogen.

8. A sulfone according to claim 1 wherein in said compound, one of $R^1$, $R^2$, $R^3$ and $R^4$ is fluoro and the remaining of $R^1$, $R^2$, $R^3$ and $R^4$ are hydrogen.

9. A sulfone according to claim 1 wherein in said compound, one of $R^1$, $R^2$, $R^3$, and $R^4$ is —$N(CH_3)_2$ and the remaining of $R^1$, $R^2$, $R^3$, and $R^4$ are hydrogen.

10. A sulfone according to claim 1 wherein in said compound, each of $R^5$ and $R^6$, independently of the other, is hydrogen, methyl, ethyl, propyl, methoxy, ethoxy, propoxy, cyclopentoxy, or cyclohexoxy.

11. A sulfone according to claim 1 wherein in said compound, $R^5$ is alkoxy and $R^6$ is alkoxy, monocycloalkoxy, or bicycloalkoxy.

12. A sulfone according to claim 1 wherein in said compound, $R^5$ is methoxy and $R^6$ is ethoxy.

13. A sulfone according to claim 1 wherein in said compound, $R^7$ is hydroxy, methyl, ethyl, phenyl, benzyl, or $NR^{8'}R^{9'}$ in which each of $R^{8'}$ and $R^{9'}$ taken independently of the other is hydrogen or methyl.

14. A sulfone according to claim 1 wherein in said compound, $R^7$ is methyl.

15. A sulfone according to claim 1 wherein in said compound, $R^7$ is $NR^8R^{9'}$ in which each of $R^{8'}$ and $R^{9'}$ taken independently of the other is hydrogen or methyl.

16. A sulfone according to claim 1 which is 2-[1-(3-ethoxy-4-methoxyphenyl)-2-methylsulfonylethyl]isoindolin-1-one, 2-[1-(3-ethoxy-4-methoxyphenyl)-2-(N,N-dimethylaminosulfonyl)ethyl]isoindolin-1-one, 2-[1-(3-ethoxy-4-methoxyphenyl)-2-methylsulfonylethyl]isoindoline-1,3-dione, 2-[1-(3-ethoxy-4-methoxyphenyl)-2-methylsulfonylethyl]-5-nitro-isoindoline-1,3-dione, 2-[1-(3-ethoxy-4-methoxyphenyl)-2-methylsulfonylethyl]-4-nitroisoindoline-1,3-dione, 2-[1-(3-ethoxy-4-methoxyphenyl)-2-methylsulfonylethyl]-4-aminoisoindoline-1,3-dione, 2-[1-(3-ethoxy-4-methoxyphenyl)-2-methylsulfonylethyl]-5-methylisoindoline-1,3-dione, 2-[1-(3-ethoxy-4-methoxyphenyl)-2-methylsulfonylethyl]-5-acetamidoisoindoline-1,3-dione, 2-[1-(3-ethyoxy-4-methoxyphenyl)-2-methylsulfonylethyl]-4-dimethylaminoisondoline-1,3-dione, 2-[1-(3-ethoxy-4-methoxyphenyl)-2-methylsulfonylethyl]-5-dimethylaminoisoindoline-1,3-dione, 2-[1-(3-ethoxy-4-methoxyphenyl)-2-methylsulfonylethyl]benzo[e]isoindoline-1,3-dione, 2-[1-(3-ethoxy-4-methoxyphenyl)-2-methylsulfonylethyl]-4-methoxyisoindoline-1,3-dione, 2-[1-(3-cyclopentyloxy-4-methoxyphenyl)-2-methylsulfonylethyl]isoindoline-1,3-dione, or 2-[1-(3-cyclopentyloxy-4-methoxyphenyl)-2-methylsulfonylethyl]-4-dimethylaminoisoindoline-1,3-dione.

17. A method of reducing undesirable levels of TNFα in a mammal which comprises administering thereto an effective amount of a compound according to claim 1.

18. A method of inhibiting PDE IV in a mammal which comprises administering thereto an effective amount of a compound according to claim 1.

19. A pharmaceutical composition comprising a quantity of a compound according to claim 1 sufficient upon administration in a single or multiple dose regimen to reduce levels of TNFα in a mammal in combination with a carrier.

* * * * *